United States Patent
Ullmann et al.

(10) Patent No.: US 9,803,198 B2
(45) Date of Patent: Oct. 31, 2017

(54) LIPOHILLIC OLIGONUCLEOTIDE ANALOGS

(71) Applicant: Miltenyi Biotec GmbH, Bergisch Gladbach (DE)

(72) Inventors: Eugen Ullmann, Bergish Gladbach (DE); Romualdus Smicius, Bergisch Gladbach (DE); Thomas Rockel, Bergisch Gladbach (DE)

(73) Assignee: Miltenyi Biotec, GmbH, Bergisch Gladbach (DE)

( * ) Notice: Subject to any disclaimer, the term of this patent is extended or adjusted under 35 U.S.C. 154(b) by 0 days.

(21) Appl. No.: 14/773,760

(22) PCT Filed: Mar. 18, 2014

(86) PCT No.: PCT/EP2014/055454
§ 371 (c)(1),
(2) Date: Sep. 9, 2015

(87) PCT Pub. No.: WO2014/147095
PCT Pub. Date: Sep. 25, 2014

(65) Prior Publication Data
US 2016/0017325 A1      Jan. 21, 2016

(30) Foreign Application Priority Data
Mar. 18, 2013    (EP) .................... 13159766

(51) Int. Cl.
*C07H 21/04*    (2006.01)
*C12N 15/113*   (2010.01)
*G01N 33/50*    (2006.01)

(52) U.S. Cl.
CPC .......... *C12N 15/113* (2013.01); *C07H 21/04* (2013.01); *G01N 33/5011* (2013.01); *C12N 2310/11* (2013.01); *C12N 2310/351* (2013.01)

(58) Field of Classification Search
CPC ..................................................... C07H 21/04
See application file for complete search history.

(56) References Cited

PUBLICATIONS

Barata et al. Cancer Treatment Reviews 50 (2016) 35-47.*

* cited by examiner

*Primary Examiner* — Kimberly Chong
(74) *Attorney, Agent, or Firm* — Jaquelin K. Spong (57) ABSTRACT

Lipophilic oligonucleotide comprising a phosphate glycerol unit containing at least one aliphatic unsaturated carbon bond according to formula (I), with Oligonucleotide an unmodified or modified nucleic acid of 2-1000 nucleotides in length R=a bond or a linker unit Y=OH, SH or NHR3 X and Z=independently O, S or NR3 R3=hydrogen or branched or unbranched and/or substituted or unsubstituted alkyl, aryl and/or alkyl aryl residue with 10 to 30 carbon atoms R1. R2 branched or unbranched and/or substituted or unsubstituted alkyl, aryl and/or alkylaryl residue with 10 to 30 carbon atoms, with the provisio that at least one of the residues R1 or R2 comprises at least one aliphatic carbon-carbon double bond Use of lipophilic oligonucleotide according to Formula I for drug discovery or for transfection of cells.

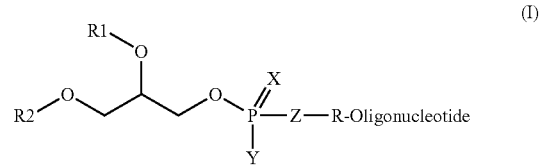

(I)

8 Claims, 4 Drawing Sheets

Figure 3:

Knock down of beta-2 microglobulin protein in human primary foreskin fibroblasts. (Example 6).

LIPOHILLIC OLIGONUCLEOTIDE ANALOGS

The invention is directed to lipophilic oligonucleotides which are chemically modified for enhanced delivery, compounds to modify lipophilic oligonucleotide, and the use of such modified lipophilic oligonucleotides for target knock-down in vivo and in vitro.

PRIOR ART

For many applications of oligonucleotides, the cellular uptake of the oligonucleotide (ODN) is the limiting factor for its intracellular activity. In particular, the efficacy of target knock-down (KD) within cells is hampered by the limited cellular uptake and intracellular availability of antisense oligonucleotides. Many attempts have been made to improve the cellular uptake of oligonucleotides aiming at efficient target KD without the use of transfection agents. However, even the most prominent lipophilic derivatives, such as cholesterol modification, did not lead to satisfying KD results.

In an effort to increase the target KD by antisense oligonucleotides, chemical modifications of antisense ODN have been studied. For example, Rait et al. disclose in Bioconjugate Chem. 2000, 11, 153-160 the modification of 1-O-hexadecylglycerol modification (Title "3'-End Conjugates of Minimally Phosphorothioate-Protected Oligonucleotides with 1-O-Hexadecylglycerol: Synthesis and Anti-ras Activity in Radiation-Resistant Cells"). In "Lipid Nucleic Acids" by Manoharan et al., Tetrahedron Letters 1995, Vol. 36, 3651-3654 and U.S. Pat. No. 4,958,013, the cholesterol modification in cell culture is described.

However, this type of modification did not significantly increase efficacy of target KD of the antisense ODN without use of transfection agents.

Transfection agents are usually highly toxic chemicals. Working with such chemicals is in general not desirable and in case of in-vivo applications not applicable. Accordingly, many attempts have been made to avoid transfection agents in favor of delivery technology. In the past 15-20 years, the intracellular delivery and KD activity of oligodeoxynucleotides have been largely dependent on the use of delivery technology like lipofection until Stein et al. disclosed in Nucleic Acids Research (2010) 38, e3 a method called "gymnosis" that does not require the use of any transfection reagent or any additives for target KD using LNA antisense. Only in the absence of transfection agents (hereinafter called "gymnotic delivery") the true effect of ODN modification on target KD can be studied and the efficacy of gymnotic delivery correlates well with the in vivo target KD (see for example Short LNA antisense ODN potently reduce ApoB mRNA and serum Cholesterol in mice and non-human primates; Straarup et al. Nucleic Acids Research (2010) 38, 7100-7111).

Certain primary cells and cell lines are difficult to transfect. Such primary cells are e.g. T cells, B cells, leukemia cells and lymphoma cells, hematopoietic stem cells, mesenchymal stem cells and monocytes; such cell lines are e.g. U937, Ramos and Raji cells.

WO 90/10448 discloses target KD by antisense oligonucleotides comprising lipophilic groups like C1-C30 alkyl or C2-C30 mono., di- or polyunsaturated alkyl groups. U.S. Pat. No. 6,395,492 describes a method of effecting cellular uptake of a compound having a plurality of linked nucleosides using a compound which has a steroid molecule, an enzyme, a peptide, a protein, or a vitamin attached to the 3' position with a linking moiety which does not include a phosphate group. Target KD by antisense oligonucleotides is furthermore known from MANOHARAN M: "Oligonucleotide conjugates as potential antisense drugs with improved uptake, biodistribution, targeted delivery, and mechanism of action", ANTISENSE & NUCLEIC ACID DRUG DEVELOPMENT, MARY ANN LIEBERT, INC., NEW YORK, US, vol. 12, 1 Jan. 2002 (Jan. 1, 2002), pages 103-128. This review article relates to oligonucleotide conjugates and refers to glycerol derivatives with one or two hexadecyl residues.

OBJECT OF THE INVENTION

KD is a promising tool for treatment of solid tumors and several diseases for example related to a dysregulated gene expression. The prior art teaches especially that oligonucleotide useful for target KD comprise conjugates with saturated groups like cholesterol (chol) and hexadecyl (hex). Accordingly, object of the invention was to provide delivery tools for antisense oligonucleotides which allows improved target knock-down (KD) within living cells without being toxic to cells and without the use of transfection agents.

It was found that target KD in the absence of any transfection reagent by gymnotic delivery in vitro is increased if the antisense oligonucleotide is derivatized with a glycerol unit containing at least one lipophilic residue comprising a at least one aliphatic unsaturated carbon bond.

First object of the invention is therefore a lipophilic oligonucleotide comprising a phosphate glycerol unit containing at least one aliphatic unsaturated carbon bond according to formula I Formula I with
Oligonucleotide=an unmodified or modified nucleic acid of 2-1000 nucleotides in length
R=a bond or a linker unit
Y=OH, SH or NHR3
X and Z=independently O, S or NR3
R3=hydrogen or branched or unbranched and/or substituted or unsubstituted alkyl, aryl and/or alkyl aryl residue with 10 to 30 carbon atoms
R1, R2=branched or unbranched and/or substituted or unsubstituted alkyl, aryl and/or alkylaryl residue with 10 to 30 carbon atoms, with the provisio that at least one of the residues R1 or R2 comprises at least one aliphatic carbon-carbon double bond In case R stands for a linker unit, R may be a bifunctional unit selected from the following group
branched or unbranched and/or substituted or unsubstituted alkyl, aryl and/or alkyl aryl residue with 1 to 100 carbon atoms
sugar
amino-, thiol-, ethylene glycol-, in particular, triethyleneglycol and hexaethyleneglycol modified C3-, C-6 and C-12-linkers optionally having two functional groups, such as e.g. amino-, thiol-, carboxyl or hydroxyl functions which allow attachment of an oligonucleotide on one side and a lipophilic residue on the other side.

reversible linker, which can de designed to undergo a chemical or enzymatic cleavage reaction, for example cleavage in acidic environment (e.g. endosomes), reductive cleavage (e.g. cytosolic cleavage) or oxidative cleavage (e.g. in liver microsomes), by enzymes like nucleases, peptidases, proteases, phosphatases, oxidases, reductases etc., disulfide-linkers, nuclease-sensitive phosphodiester linkages.

Since the residue Y may stand for OH, SH or NHR3, the phosphate glycerol unit containing at least one aliphatic unsaturated carbon bond according to formula I can be deprotonated to form an anion. The present invention relates to any anionic variant of the phosphate glycerol unit according to formula I too, whereas the counter ion is of no particular importance and may be for example, sodium, potassium or any amine.

R1 and R2 stand for the same or a different residue. The unsaturated lipophilic residues R1 and R2 may be mono-unsaturated, bis-unsaturated, tris-unsaturated and poly-unsaturated lipophilic residues, examples being:

Monounsaturated: palmitoeyl alcohol (cis-9-hexadecen-1-ol), elaidyl alcohol (trans-9-octadecen-1-ol), oleyl alcohol (cis-9-octadecen-1-ol), ricinoleyl alcohol, erucyl alcohol, brassidyl alcohol, phytol).

Bis-unsaturated: linoleyl alcohol (cis,cis-9,12-octadecadien-1-ol), elaidolinoleyl alcohol (trans,trans-9,12-octadecadien-1-ol), geraniol (trans-3,7-dimethyl-2,6-octadien-1-ol), bombykol (trans-10,cis-12-hexadecadien-1-ol).

Tris-unsaturated: linolenyl alcohol (cis,cis,cis-9,12,15-octadecatrien-1-ol), elaidolinolenyl alcohol (trans,trans,trans-9,12,15-octadecatrien-1-ol), farnesol ((trans,trans-2,6)-3,7,11-trimethyl-2,6,10-dodecatrien-1-ol).

Poly-unsaturated: geranylgeraniol (tetra), geranylfarnseol (penta), retinol (penta), solenasol (nona), spadicol (deca).

Surprisingly it was found, that the oligonucleotides having lipophilic residues based on substituted glycerol are even more active as KD agents if two of the hydroxy groups of glycerol are substituted by lipophilic residue (e.g. as in formulas III and IV) as compared to the mono-substituted glycerol analog formula V.

Especially suitable are compounds wherein at least one of the lipophilic residues contains a non-saturated carbon bond and has more than 20 C-atoms.

Specific examples for phosphate glycerol units according to the invention are the dierucylglycerol (dier) derivative as shown by formula III and the mixed erucyl-myristyl (ermy) derivative as shown by formula IV. The dier derivative III was also tested in vivo where it showed excellent KD of ApoB after i.v. administration of an ApoB LNA gapmer having a dier moiety at its 5'-end. LNA is Locked Nucleic Acid (2'-O, 4'-C-methylene bridged nucleoside).

In formula II, IV and V R, X, Y, Z, R1, R2 and R3 have the same meaning as in Formula I and ODN stands for Oligonucleotide with the same meaning as in Formula I.

Further examples of lipophilic residues R1, R2 containing a non-saturated carbon chain suitable to produce lipophilic oligonucleotides of the invention are:

Palmitoeyl alcohol (cis-9-hexadecen-1-ol)-$CH_3(CH_2)_5$—CH=CH—$(CH_2)_8OH$

Elaidyl alcohol (trans-9-octadecen-1-ol)-$CH_3(CH_2)_7$—CH=CH—$(CH_2)_8OH$

Oleyl alcohol (cis-9-octadecen-1-ol)-$CH_3(CH_2)_7$—CH=CH—$(CH_2)_8OH$

Linoleyl alcohol (cis,cis-9,12-octadecadien-1-ol)-$CH_3(CH_2)_4$—CH=CH—$CH_2$—CH=CH—$(CH_2)_8OH$

Elaidolinoleyl alcohol (trans,trans-9,12-octadecadien-1-ol)-$CH_3(CH_2)_4$—CH=CH—$CH_2$—CH=CH—$(CH_2)_8OH$ Linolenyl alcohol (cis,cis,cis-9,12,15-octadecatrien-1-ol)-$CH_3CH_2$—CH=CH—$CH_2$—CH=CH—$CH_2$—CH=CH—$(CH_2)_8OH$ Elaidolinolenyl alcohol (trans,trans,trans-9,12,15-octadecatrien-1-ol)-$CH_3CH_2$—CH=CH—$CH_2$—CH=CH—$CH_2$—CH=CH—$(CH_2)_8OH$ Further examples for lipophilic residues R1, R2 containing a saturated carbon chain, but not limited to, are e.g. capric alcohol (1-decanol), undecyl alcohol (1-undecanol), lauryl alcohol (1-dodecanol), tridecyl alcohol (1-tridecanol), myristyl alcohol (1-tetradecanol), pentadecyl (1-pentadecanol), cetyl alcohol (1-hexadecanol), heptadecyl alcohol (1-heptadecanol), stearyl alcohol (1-octadecanol), nonadecyl alcohol (1-nonadecanol), arachidyl alcohol (1-eicosanol).

All compounds can be coupled via the hydroxyl group to the phosphate unit.

Synthesis of Lipophilic Oligonucleotides

Another object of the invention is a method for the preparation of oligonucleotides of formula I, wherein a compound Oligonucleotide-R—OH is coupled with a phosphate glycerol unit containing one lipophilic residue according to formula II With
R5, R6=Methyl, Ethyl, Propyl, isopropyl, Butyl residue, or R1 and R2 forming a cyclic aliphatic residue
R4=protecting group, selected from the group of alkyl, substituted alkyl, alkylaryl, β-cyanoalkyl, β-phenylethyl
R, R1, R2 the same meaning as in Formula I
and subsequently oxidized and deprotected to yield oligonucleotides of formula I.

In principle any protecting group can be used at the phosphate which prevents undesirable side reaction at the phosphorus during the preparation of the lipophilic conjugate, but which can be cleaved after successful preparation of the oligonucleotide conjugate without side reactions at other positions of the molecule to render the oligonucleotide lipophilic conjugate in its desired unprotected form.

In a preferred embodiment, the protecting group can be cleaved in a β-elimination reaction, such as the β-cyanoethyl protecting group. The β-cyanoethyl group can also be substituted, e.g. by a C1-C6 alkyl residue or by one or more halogen atoms. Another preferred protecting group is a β-phenylethyl residue, which can also be cleaved in a β-elimination reaction using a suitable base, such as e.g. DBU. Substituted β-phenylethyl protecting groups are e.g. p-nitro- or o-nitro-β-phenylethyl. In another preferred embodiment, the protecting group is an alkyl group, for example a methyl group which can be cleaved with ammonia or other bases.

The method of the invention is shown by way of example in scheme I:

Scheme I

The activation, coupling, oxidization and deprotection steps are performed with common methods known to the person skilled in the art.

In a further embodiment of the method of the invention, the phosphate glycerol unit containing one lipophilic residue according to formula II for preparation of the oligonucleotides may have the structure of formula VI and VII With
R5, R6=Methyl, Ethyl, Propyl, isopropyl, Butyl residue, or R1 and R2 forming a cyclic aliphatic residue
R4=protecting group, selected from the group of alkyl, substituted alkyl, alkylaryl, β-cyanoalkyl, β-phenylethyl A preferred phosphate glycerol unit containing one lipophilic residue comprising only one aliphatic unsaturated carbon bond has the structure according to formula VIII with DMTr=4,4'-Dimethoxytrityl residue Formula VIII Oligonucleotides The term oligonucleotide in formula I stands for an unmodified or modified nucleic acid of 2 to 1000 nucleotides (nt) in length. The length of the oligonucleotide depends to a great extent on the use and concept as inhibitor or agonist. The use of the lipophilic oligonucleotide as antisense oligonucleotide may comprise oligonucleotides of a length of 6 to 30 nucleotides. In a preferred embodiment, the oligonucleotide is a lipophilic antisense oligonucleotide with a length of 10 to 20 nucleotides. However, the lipophilic nucleic acid can also be very long, such as several hundred to thousands nt in length. Long lipophilic nucleic acids may not be prepared directly using online synthesis. Instead, short lipophilic oligonucleotides are prepared by online synthesis and are then ligated in a chemical or enzymatic ligation reaction to long nucleic acids resulting in long lipophilic nucleic acids.

The glycerol phosphate comprising the lipophilic residues can be linked directly (R is a bonding) or through a linker unit R, as for example an organic radical with 1 to 100 carbon atoms, or any of the following molecules to the oligonucleotide. The lipophilic residue can be attached to the phosphate, the sugar or to the nucleobase of the nucleotides.

The lipophilic residue can be attached anywhere within the nucleic acid sequence. However, the lipophilic residue is preferably directly linked to either the 5'-terminus or the 3'-terminus of an oligonucleotide. The lipophilic residue can also be part of a secondary structure of the nucleic acid. An example for this situation would e.g. be an oligonucleotide with a hairpin structure, where the lipophilic residue is attached to the single-stranded loop region of the hairpin. Hairpin structures of nucleic acids can form spontaneously if the sequence contains e.g. inverted repeats or palindromic regions, respectively. Hairpin structures are e.g. used in siRNA and occasionally also in antisense oligonucleotides. In double-stranded siRNA, only one strand may be modified with a lipophilic residue or alternatively both strands of the siRNA can bear a lipophilic residue. Both strands can comprise identical lipophilic residues or different residues.

Linkers are organic molecules which serve the purpose to attach the lipophilic residue at a defined distance to the oligonucleotide. The length of the linker and steric dimensions determine the distance between the lipophilic residue and the oligonucleotide and steric orientation of the lipophilic conjugate. Linkers can be e.g. abasic residues or nucleobase containing residues. Abasic residues are frequently named "modifiers", since the modifiers introduce or allow to introduce modifications. The skilled person will know e.g. various amino-modifiers, thiol-modifiers, ethylene glycol modifiers, in particular, triethyleneglycol and hexaethyleneglycol modifiers, but also long chain polyethethyleneglycol modifiers. Known linkers are e.g. also C3-, C-6 and C-12-linkers having two functional groups, such as e.g. amino-, thiol-, carboxyl or hydroxyl functions which allow attachment of an oligonucleotide on one side and a lipophilic residue on the other side.

It is furthermore possible to place a reversible linker R between the oligonucleotide and the lipophilic residue. A reversible linker can de designed to undergo a chemical or enzymatic cleavage reaction. Chemical reactions involve e.g. cleavage in acidic environment (e.g. endosomes), reductive cleavage (e.g. cytosolic cleavage) or oxidative cleavage (e.g. in liver microsomes). The cleavage reaction can also be initiated by a rearrangement reaction. Enzymatic reactions can e.g. include nucleases, peptidases, proteases, phosphatases, oxidases, reductases etc. It was found that disulfide-linked lipophilic 5'-substitutions appear to be more effective in ApoB KD than the directly linked analog. The simplest reversible linker, which is cleaved enzymatically, is a stretch of nucleotides linked by nuclease-sensitive phosphodiester linkages. In serum there are mainly exonucleases, such as 3'-exonucleases. In organs and inside cells, there are also endonucleases. Therefore, a lipophilic residue attached to the stabilized oligonucleotide via nuclease-sensitive phosphodiester nucleotides, would have reasonable stability in serum, but would be cleaved in organs or after uptake into cells of the organs. A preferred location of lipophilic oligonucleotides is the liver, but also kidney, lymph nodes, muscle and bone marrow.

Since the lipophilic conjugate is stable in plasma, the linker can also be designed to undergo an organ-specific cleavage by appropriate linker chemistry. For certain targets, which are expressed in various tissues, only the knock-down in liver may be desirable, as knock-down in other organs may lead to undesired side effects. Thus, linkers susceptible to liver-specific enzymes, such as pyrrolase (TPO) and glucose-6-phosphatase (G-6-Pase), can be engineered in, so that the antisense effect would be observed in the liver mainly. Alternatively, linkers not susceptible to liver enzymes but to kidney-specific enzymes, such as gamma-glutamyl transpeptidase, can be engineered in, so that the antisense effect would be observed in the kidney mainly. Further, testine specific peptidases cleaving Phe-Ala and Leu-Ala could be considered after oral application. Similarly, by placing an enzyme recognition site into the linker, which is recognized by an enzyme over-expressed in tumors, such as plasmin (e.g. PHEA-D-Val-Leu-Lys recognition site), tumor-specific knock-down should be feasible. By selecting the right enzyme recognition site in the linker, specific cleavage and knock-down should be achievable in many organs. In addition, the linker can also contain a targeting signal, such as N-acetyl galactosamine for liver targeting, or folate, vitamine A or RGD-peptide in the case of tumor targeting.

The chemistry of the oligonucleotide is not limited to LNA or LNA gapmers, since the lipophilic conjugate concept is expected to work with any chemistry, for which the target knock-down using a non-conjugated antisense ODN is effective. This includes for instance ENA, HNA, fluoro-HNA, FANA, 2'-modified analogs as MOE, phosphate-modified analogs as phosphoramidate, morpholinos, base-modified analogs, such as G-clamps and 5-alkinyl-pyrimidines. The antisense oligonucleotides of this invention can support an RNase H mechanism, but can also work by steric blocking only, which also includes transcriptional gene silencing and transcriptional gene activation. All state-of-the-art chemistry known from the antisense oligonucleotide field should be applicable to the lipophilic conjugation.

In addition, the invention relates to derivatives of the oligonucleotides, e.g. their salts and more specifically to their physiologically tolerated salts. Salts and physiologically tolerated salts are e.g. described in Remington's Pharmaceuticals Science (1985) Mack Publishing Company, Easton, Pa. (page 1418). Derivatives are modified oligonucleotides which have one or more modifications in the molecule which are usually different from natural nucleic acids, but may also occur in nature, such as 2'-O-methylribose (sugar modification) or 5-methylcytosine (nucleobase modification). Modifications are introduced into oligonucleotides aiming at improvement of their properties, e.g. to increase to increase of its binding affinity to a complementary nucleic acid, such as mRNA, or to enhance their metabolic stability against nucleases or to modulate or target the cellular uptake.

Furthermore, the present invention relates to oligonucleotides having one or more chemical modifications in comparison to a "natural" DNA, which is composed of the nucleotides A, T, C and G linked via phosphodiester internucleoside bridges. The oligonucleotides may have one or more modifications of the same type and/or modifications of a different type, where each type of modification can independently be selected from the types of modifications known to the skilled person to be used for modifying oligonucleotides. Examples of chemical modifications known to the skilled person are for example described in Uhlmann and Peyman (1990) Chemical Reviews 90, 543; Goodchild J (1990) Bioconjugate Chem 1, 165; Kurreck (2003) Eur. J. Biochem. 270, 1628; Aboul-Fadl (2005) Curr. Med. Chem., 12, 2193; Bennett and Swayze (2009) Ann. Rev. Pharmacol. Toxicol. 50, 259).

In one embodiment, the invention relates to a lipophilic oligonucleotide according to formula I which comprises one or more modifications and wherein each modification is independently selected from A) the replacement of a phosphodiester internucleoside bridge by a modified internucleoside bridge,
B) the replacement of a deoxy sugar unit by a modified sugar unit,
C) the replacement of a natural nucleoside base by a modified nucleoside base,
D) the introduction of a 3'-3', a 2'5' and/or a 5'-5' linkage, E) the conjugation to a molecule which modulates the properties of the oligonucleotide, and/or F) the replacement of a nucleotide by a non-nucleotidic moiety (e.g. linker)

A)

Replacement of a phosphodiester internucleoside bridge by a modified internucleoside bridge are for example selected from the following modifications: phosphorothioate, phosphorodithioate, phosphoramidate, boranophosphate, phosphate-(C1-C21)-O-alkyl ester, phosphate-[(C6-C12)aryl-((C1-C21)-O-alkyl]ester, (C1-C8)alkyl-phosphonate and/or (C6-C12)-arylphosphonate bridges. The replacement of a nonchiral phosphodiester bridge by a modified bridge mostly results in diastereoisomers. In a preferred embodiment of this invention, the replacement involves a phosphonoacetate linkage (U.S. Ser. No. 09/691,824, PCT/US01/32465). The oligomers of this invention can be diastereoisomeric pure (Rp or Sp) or a racemic mixture of the diastereoisomers. The replacement of a phosphodiester bridge by a dephospho bridge (dephospho bridges are described, for example, in Uhlmann, E. and Peyman, A. in "Methods in Molecular Biology", Vol. 20, "Protocols for Oligonucleotides and Analogs", S. Agrawal, Ed., Humana Press, Totowa 1993, Chapter 16, 355ff). The dephospho bridges may be selected e.g. from formacetal, 3-thioformacetal, methylhydroxylamine, oxime, methylenedimethyl-hydrazo, dimethylenesulfone and/or silyl groups.

Specific dephosphoso analogs are e.g. morpholino-oligomers (as described, for example, in E. P. Stirchak et al., Nucleic Acids Res. 17 (1989) 6129) and polyamide nucleic acid ("PNA") (as described for example, in P. E. Nielsen et al., Bioconj. Chem. 5 (1994) 3 and in EP 0672677 A2), that is e.g. the replacement by a PNA backbone unit, e.g. by 2-aminoethylglycine. Another dephospho analog are the so-called Ugi-Oligomers. Chimeric molecules comprising PNA and DNA or modified DNA are also within the scope of this invention.

B)

Replacement of β-D-2'-deoxyribose by a modified sugar unit, wherein the modified sugar unit is for example selected from β-D-ribose, [alpha]-D-2'-deoxyribose, L-2-deoxyribose, 2'-fluoro-2'-deoxyribose, 2'-O—(C1-C6)alkyl-ribose, preferably 2'-O—(C1-C6)alkyl-ribose is 2'-O-methylribose, 2'-O—(C2-C6)alkenyl-ribose, 2'-[O—(C1-C6)alkyl-O—(C1-C6)alkyl]-ribose, 2'-O-ethoxymethyl (MOE), 2'-amino-2'-deoxyribose, 2'-azido-2'-deoxyribose, β-D-xylofuranose, arabinofuranose, 2'-fluoro-arabinofuranose (FANA) (Lon et al. 2002, Biochem 41, 3457), 2,4-dideoxy-[beta]-D-erythro-hexo-pyranose, and carbocyclic (described, for example, in Froehler, J. Am. Chem. Soc. 114 (1992) 8320) and/or open-chain sugar analogs (described, for example, in Vandendriessche et al., Tetrahedron 49 (1993) 7223) and/or bicyclosugar analogs (described, for example, in M. Tarkov et al., Helv. Chim. Acta 76 (1993) 481). A preferred embodiment involves the replacement of β-D-2'-deoxyribose by a bicyclic nucleic acid analog (BNA), e.g. LNA, amino-bridged LNA, ENA and c-Et (Bennett and Swayze 2009, Koizumi 2006, Curr Opin Mol Therapy 8, 144). In another embodiment the sugar replacement involves a six-membered ring sugar, e.g. cyclohexyl nucleic acid (CAN) or hexitol nucleic acids (HNA).

C)

Another embodiment of this invention involves the replacement of a natural nucleobase by a modified nucleobase, wherein the modified base is for example selected from uracil, hypoxanthine, 5-(hydroxymethyl)uracil, N2-Dimethylguanosine, 5-(hydroxymethyl)uracil, 5-aminouracil, pseudouracil, dihydrouracil, 5-fluorouracil, 5-fluorocytosine, 5-chlorouracil, 5-chlorocytosine, 5-bromouracil, 5-iodouracil, 5-bromocytosine, 2,4-diaminopurine, 8-azapurine, a substituted 7-deazapurine, preferably a 7-deaza-7-substituted and/or 7-deaza-8-substituted purine or other modifications of a natural nucleoside bases, e.g. modified nucleoside bases (described in EP 0 710 667 A2 and EP 0 680 969 A2). Particularly preferred nucleobase replacements involve 5-substituted pyrimidines, such as 5-propynyluracil, 5-propynylcytosine, 5-hexynyl pyrimidines and 5-octadienyl pyrimidines. Another preferred modification involves the replacement by a so-called G-clamp (WO99/24452), which dramatically improves binding affinity of the oligonucleotide to complementary nucleic acids.

Another embodiment of this invention is the conjugation of the oligonucleotide to a 2'5'-linked oligoadenylate, preferably via an appropriate linker molecule, wherein the 2'5'-linked oligoadenylate is for example selected from 2'5'-linked triadenylate, 2'5'-linked tetraadenylate, 2'5'-linked pentaadenylate, 2'5'-linked hexaadenyltat or 2'5'-linked heptaadenylat molecules and derivatives thereof, and wherein an example for an appropriate linker is triethyleneglycol and wherein the 5-end of the 2'5'-linked oligoadenylate preferably bears a phosphate, diphosphate or triphosphate residue in which one or several oxygen atoms can be replaced e.g. by sulfur atoms, wherein the substitution by a phosphate or thiophosphate residue is preferred. The 2'5'-linked oligoadenylate is able to recruit RNase L which helps in the degradation of mRNA (Torrence et al., Proc. Natl. Acad. Sci. U.S.A. (1993) 90, 1300).

D)

Another embodiment involves the introduction of a 3'-3' and/or a 5'-5' inversion into the oligonucleotide, wherein this type of chemical modification is known to the skilled person and is described, for example, in M. Koga et al, J. Org. Chem. 56 (1991) 3757, EP 0 464 638 and EP 0 593 901. This type of linkage is also being used to generate homo-dimers or hetero-dimers of oligonucleotides. For instance, 3'3'-linked homo-dimers of CpG oligonucleotides are more active than 5'5'-linked dimers or the corresponding monomeric CpG oligonucleotide.

E)

In another embodiment of the invention, the oligonucleotide contains a conjugated molecule which determines the properties of the oligonucleotide. Such conjugated molecules may modulate the properties of cellular uptake, in particular targeted delivery. In latter case, the conjugated molecule can e.g. be folate which targets the oligonucleotide to cells expressing the folate receptors. Other conjugated molecules comprise vitamins, such as vitamin A, B and D. Other conjugate molecules comprise peptides, such as cell penetrating peptides, RGD peptides or nuclear targeting peptide sequences. Other conjugated molecules are antibodies specific to certain cell surface proteins, such as receptors.

F)

Replacement of a nucleotide by a non-nucleotidic moiety is another embodiment of this invention. The non-nucleotidic residue may be a universal base, an abasic spacer or any organic radical, which does not comprise a nucleobase.

In a special embodiment of the invention, at least one or more internucleoside bridges within the oligonucleotide sequence are modified, preferably with phosphorothioate. In an all-phosphorothioate oligonucleotide, all phosphodiester internucleoside bridges are modified by phosphorothioate. One embodiment of the invention relates to an oligonucleotide in which not all phosphodiester internucleoside bridges are modified uniformly with phosphorothioate (phosphorothioate internucleoside bridges). Preferably, at least one internucleoside bridge has a different type of modification or is not modified. The bridge may also involve phosphonoacetates.

In another preferred embodiment of the invention only particular positions within an oligonucleotide sequence are modified (e.g. partially modified oligonucleotide). Partially modified oligonucleotides are also named minimal modified oligonucleotides in some documents. Within the sequence a modification can be located at particular positions (at particular nucleotides, at particular nucleosides, at particular nucleoside bases, at particular internucleoside bridges).

In a particular embodiment of the invention, the oligonucleotide is prepared by only replacing some of the phosphodiester bridges with modified internucleoside bridges, e.g. phosphorothioate bridges. In particular, the invention comprises such oligonucleotides which are only modified to a certain extent. The principle of partially modified oligonucleotides is described in A. Peyman, E. Uhlmann, Biol. Chem. Hoppe-Seyler, 377 (1996) 67-70 and in EP 0 653 439.

In a particular embodiment, the invention relates to an oligonucleotide, wherein the terminal 1 to 5 nucleotide units at the 5' end and/or at the 3' end of the oligonucleotide are protected by modified nucleosides. This is also called the "gap-mer" design in case of antisense oligonucleotides (Bennett and Swayze 2009; Stanton et al. 2012, Nucleic Acids Therapeutics 22, 344). The term "gapmer" or "gapped oligomeric compound" refers to a chimeric oligomeric nucleic acid comprising a central region (a "gap") and a region on either side of the central region (the "wings"), wherein the gap comprises at least one modification that is different from that of each wing. In the gap-mers, the unmodified middle part of the oligonucleotides allows for an RNase H cleavage after binding of the oligomer to complementary RNA. The possibility of RNase H cleavage is thought to strongly improve potency of antisense oligonucleotides. In another embodiment, the invention relates to an oligonucleotide, in which the modifications are placed irregularly, such as in so-called "mix-mers". Preferred antisense gap-mers have 2 to 3 sugar modified nucleoside residues at the 5' and/or 3'-end of the oligonucleotide. In another preferred embodiment, the invention relates to oligonucleotides having 2 to 3 bicyclic LNA, ENA or c-Et nucleotides at the 5' and/or 3'-end.

In another embodiment, the invention relates to an oligonucleotide, wherein at least one internal pyrimidine nucleoside and/or an internucleoside bridge located at the 5'end of this pyrimidine nucleoside and/or located at the 3'end of this pyrimidine nucleoside is modified.

In another embodiment of the invention, the oligonucleotides can have in addition to one type of modification, also other types of modification. For example, a phosphorothioate modified oligonucleotide may also have additional modifications, e.g. modification of a β-D-2'-deoxyribose or modification of the nucleobase. In these multiple modified oligonucleotide derivatives, β-D-2'-deoxyribose is preferably replaced by 2'-fluoro-2'-deoxyribose, 2-O—(C1-C6) alkylribose, 2'-O-methylribose, LNA, ENA or c-Et.

Through the lipophilic modification of oligonucleotides, pharmacodynamic properties, such as e.g. the organ distribution and plasma half-life, can be improved in addition to the cellular uptake of oligonucleotides. Therefore, the lipophilic modifications of this invention can be used to improve the properties of many nucleic acid therapeutics, including e.g. antisense oligonucleotides, siRNA, aptamers, decoy oligonucleotides, antagomirs, splicing correction oligomers, or Toll-like receptor agonists and antagonists.

For example, the oligonucleotides of Tables 1a are coupled to the lipophilic phosphate glycerol units mentioned above are especially suitable as antisense oligonucleotides for target KD.

TABLE 1a (dN stands for 2'-deoxynucleotide (N = A, G, C, and T), βN is LNA nucleoside (N = A, G, Z, and T, wherein Z is 5-methyl cytosine, (*) is phosphorothioate and (-) is phosphodiester internucleotide linkage. All other abbreviations see Table 1b)

| Code | oligonucleotide |
|---|---|
| 101420 | Hex-βG*βZ*dA*dT*dT*dG*dG*dT*dA*dT*βT*βZ*βA |
| 105058 | Dier-βG*βZ*dA*dT*dT*dG*dG*dT*dA*dT*βT*βZ*βA |
| 105059 | Ermy-βG*βZ*dA*dT*dT*dG*dG*dT*dA*dT*βT*βZ*βA |
| 105551 | Chol-βG*βZ*dA*dT*dT*dG*dG*dT*dA*dT*βT*βZ*βA |
| 105553 | Hex-SS-βG*βZ*dA*dT*dT*dG*dG*dT*dA*dT*βT*βZ*βA |
| 105554 | Bat-SS-βG*βZ*dA*dT*dT*dG*dG*dT*dA*dT*βT*βZ*βA |
| 105556 | Dier-SS-βG*βZ*dA*dT*dT*dG*dG*dT*dA*dT*βT*βZ*βA |
| 105557 | Ermy-SS-βG*βZ*dA*dT*dT*dG*dG*dT*dA*dT*βT*βZ*βA |
| 105558 | dRVitA-βG*βZ*dA*dT*dT*dG*dG*dT*dA*dT*βT*βZ*βA |
| 105559 | dRVitA-SS-βG*βZ*dA*dT*dT*dG*dG*dT*dA*dT*βT*βZ*βA |
| 105560 | dRVitE-βG*βZ*dA*dT*dT*dG*dG*dT*dA*dT*βT*βZ*βA |
| 105561 | dRVitE-SS-βG*βZ*dA*dT*dT*dG*dG*dT*dA*dT*βT*βZ*βA |
| 105754 | Dier-βZ*βG*dT*dC*dT*dA*dT*dG*dT*dA*βT*βA*βG (102103 seq) |
| 105755 | DMTr-βG*βZ*dA*dT*dT*dG*dG*dT*dA*dT*βT*βZ*βA |
| 105756 | DMTr-SS-βG*βZ*dA*dT*dT*dG*dG*dT*dA*dT*βT*βZ*βA |
| 105757 | DMTr-L-βG*βZ*dA*dT*dT*dG*dG*dT*dA*dT*βT*βZ*βA |
| 104454 | pyr-βG*βZ*dA*dT*dT*dG*dG*dT*dA*dT*βT*βZ*βA |
| 105872 | pyr-SS-βG*βZ*dA*dT*dT*dG*dG*dT*dA*dT*βT*βZ*βA |
| 105873 | pyr-dT-dT-dT-βG*βZ*dA*dT*dT*dG*dG*dT*dA*dT*βT*βZ*βA |
| 105874 | pyr-βZ*βG*dT*dC*dT*dA*dT*dG*dT*dA*βT*βA*βG |

TABLE 1b

| Hex | Hexadecyl-glycerol | |
|---|---|---|
| Dier | Dierucyl-glycerol | |

TABLE 1b-continued

| | | |
|---|---|---|
| Erny | Erucyl-myristyl-glycerol | (structure: CEPO-P(N(i-Pr)₂)-O-CH₂-CH(O-C₁₄H₂₉)-CH₂-O-C₁₂H₂₄-C₈H₁₇) |
| Chol | Cholesterol | |
| Bat | Octadecyl-glycerol (batyl alcohol) | (structure: DMTrO-CH₂-CH(O-P(N(Pr-i)₂)(OCEP))-CH₂-O-C₁₈H₃₇) |
| DMTr | Dimethoxy-trityl | (structure: bis(4-methoxyphenyl)phenylmethyl) |
| Eru | cis-13-Doco-senol (erucyl alcohol) | (structure: CEPO-P(N(i-Pr)₂)-O-C₁₂H₂₄-C₈H₁₇) |
| Myr | 1-Tetradeca-nol (myristyl alcohol) | (structure: CEPO-P(N(i-Pr)₂)-O-C₁₄H₂₉) |
| Pyr | pyrene | (structure: pyrenyl-CH₂-N-pyrrolidine-O-P(N(Pr-i)₂)(OCEP)) |
| SS | disulfid linker | DMTrO(CH₂)₆—SS—(CH₂)O₆—P(N(i-Pr)₂)(OCEP) |
| dRVitA | vitamine A | (structure: DMTrO-deoxyribose(OCEP-P-N(Pr-i)₂)-O-C₆H₁₂NH-C(O)-OCH₂-retinyl) |

TABLE 1b-continued dRVitE    vitamine E

Surprisingly, the type of chemical modification strongly impacts the KD activity of the antisense oligonucleotide. We tested various lipophilic derivatives of the same oligonucleotide for the efficacy of target KD. Surprisingly, we found that the frequently used cholesterol modification is by far not the most efficient modification, but only the glycerol-based alkyl chains having two lipophilic tails, in which at least one lipophilic tail contains at least a single unsaturated carbon-carbon bond, such as e.g. the "dier" and "ermy" residues, are very effective to increase the KD potency of the antisense oligonucleotide.

INDUSTRIAL APPLICABILITY

In the case of antisense oligonucleotides and siRNA, the lipophilic oligonucleotide may be directed against any target mRNA whose KD may result in a beneficial effect, e.g. in a therapeutic effect. Therefore, the lipophilic oligonucleotides of this invention may be used in the therapy of many diseases, including cancer, viral diseases, metabolic diseases, autoimmune diseases, inflammation, neurological diseases as well as muscular diseases, to name but a few.

In a preferred embodiment, the lipophilic antisense oligonucleotide of this invention is directed against a target relevant in metabolic diseases, such as e.g. liver diseases. In a preferred embodiment, the lipophilic antisense oligomer is directed against a liver target, such as e.g. ApoB or ApoC.

In another embodiment, the lipophilic antisense oligonucleotide of this invention is directed against a target relevant for MHC composition, e.g. beta-2 microglobulin. In a further embodiment, the lipophilic antisense oligonucleotide is directed against targets related to MHC-associated diseases.

By selecting appropriate sequences against various cancer or tumor related targets, the present invention is also suitable for cancer treatment. Thus, it is possible to use oligonucleotide sequences which are directed against targets responsible for the development or growth of cancers, such as: oncoproteins, e.g. c-myc, N-myc, c-myb, c-fos, c-fos/jun, PCNA, p120, EJ-ras, c-Ha-ras, N-ras, rrg, bcl-2, bcl-x, bcl-w, cdc-2, c-raf-1, c-mos, c-src, c-abl, c-ets, against cellular receptors, such as EGF receptor, Her-2, c-erbA, VEGF receptor (KDR-1), retinoid receptors, against protein kinases, c-fms, Tie-2, c-raf-1 kinase, PKC-alpha, protein kinase A (R1 alpha), against growth factors, such as bFGF, VEGF, EGF, HB-EGF, PDGF and TGF-β, against cytokines, such as IL-10, against cell cycle proteins, such as cyclin-E, against tumor proteins, such as MAT-8, or against inhibitors of tumor suppressor genes such as MDM-2. Also of use are antisense or siRNA sequences directed against components of spindle formation, such as eg5 and PLK1, or against targets to suppress metastasis, such as CXCR4. Of use are antisense sequences directed against factors which suppress apoptosis, such as survivin, bcl-2, stat3 and hdm2, or which suppress the expression of multiple drug resistance genes, such as MDR1 (P-glycoprotein).

The lipophilic conjugation can also be applied to micro RNA (miRNA) which are single-stranded RNA molecules of about 21-23 nucleotides in length regulating gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to down-regulate gene expression. It appears that many miRNA sequences discovered in the human genome contribute to the development of cancer. Some miRNAs are significantly deregulated in cancer. Further, miRNA which is over-expressed (e.g. TGF-β2 receptor, RB1 and PLAG1) leading to tumor growth can be down-regulated using antisense approaches as described before. A miRNA expression signature of human solid tumors defining cancer gene targets has recently been reported (Volinia et al. PNAS (2006) 103, 2257-61).

The lipophilic nucleic acid analogs provided herein can also be applied in the areas of drug discovery and in particular for target validation. In a special embodiment, the lipophilic compounds and targets identified herein may be used to study the relationships between proteins and a disease state, phenotype, or condition. The lipophilic nucleic acid may be used by those of ordinary skill to study and understand the function of particular genes or to distinguish between functions of various members of a biological pathway which will finally allow to develop new chemical entities or drugs which may be different from nucleic acid therapeutics, e.g. they may be small molecule therapeutics.

In another preferred embodiment, the oligonucleotides are used to treat primary cells or cell lines which are difficult to transfect. Such primary cells are e.g. T cells, B cells, leukemia cells and lymphoma cells, HSCs (CD34+, CD133+ cells), MSCs and Monocytes. Such cell lines are e.g. U937, Ramos and Raji cells.

The lipophilic oligonucleotide according to the invention may furthermore be used
  as drug or within a therapy against components of spindle formation, against targets to suppress metastasis, against factors which suppress apoptosis, or factors suppressing the expression of multiple drug resistance genes.
  for inhibition of gene expression in the liver, for inhibition of gene expression in hepatocytes, for inhibition of gene expression of ApoB, for inhibition of gene expression, where the oligonucleotide is an antisense oligonucleotide.

for inhibition of gene expression, where the oligonucleotide is an antisense oligonucleotide and the chemical modification comprises LNA and/or DNA.

for inhibition of gene expression relevant for MHC composition and/or against beta-2 microglobulin and/or against targets related to MHC-associated diseases

EXAMPLES

Example 1: Synthesis of Phosphate Glycerol Units with Dierucyl or Erucyl/Myristyl Residues

1,2-O-Dierucyl- and 1-O-Erucyl-2-O-myristyl-rac-glycerol-3-O-(2-cyanoethyl)-N,N-diisopropylphosphoramidites To a solution of 0.5 g 1,2-O-Dierucyl-rac-glycerol (0.71 mmol, 705 g/mol) or 1-O-Erucyl-2-O-myristyl-rac-glycerol (0.84 mmol, 595 g/mol) and 0.2 ml triethylamine (0.143 g, 1.42 mmol, 0.726 g/ml, 101 g/mol) in 15 mL of CH2Cl2 pre-cooled to 0° C. (ice-water bath) 0.24 mL chloro-2-cyanoethyl-N,N-diisopropylphosphoramidite (0.252 g, 1.06 mmol, 1.061 g/ml, 236.68 g/mol) was added. The reaction mixture was allowed to warm (slowly) while stirring and further was stirred for 3 h at room temperature. Then the reaction mixture was diluted with 60 mL of $CH_2Cl_2$, washed with saturated $NaHCO_3$ (2×150 mL), and then with saturated NaCl (1×150 mL), dried over $Na_2SO_4$, and evaporated to dryness. The product is suitable for further use in oligonucleotide synthesis.

Example 2: Synthesis of 1-O-DMTr-3-O-erucyl-rac-glycerol

To a solution of 0.95 g (2.38 mmol, 399 g/mol) 1-O-erucyl-rac-glycerol and in 10 ml diethyl ether 0.89 g (2.62 mol, 338.8 g/mol) 4,4'-dimethoxytrityl chloride was added and then, while stirring resulted suspension, 0.36 ml (0.265 g, 2.62 mmol, 0.726 g/ml, 101 g/mol) triethylamine was added dropwise. The reaction mixture were stirred overnight (18 h) at room temperature. Then the mixture was diluted with 30 ml of diethyl ether, filtered, precipitate washed with diethyl ether (3×20 ml). TLC showed main spot with =0.2 (AcOEt/hexane=1:5), =0.5 (AcOEt/hexane=2:5), and minor spots with Rf=0.25 and 0.1, =0.55 and 0.1-0.3 (last ones are very UV weak). After evaporation to dryness the mixture was purified twice by column chromatography using 40 g and 24 g columns with 40 m silica-gel particles 0-100% hexane-AcOEt as eluent. Yield: 1.3 g (78%), Rf=0.3 (AcOEt/hexane=1:5), =0.5 (AcOEt/hexane=2:5).

Example 3: Synthesis of 1-O-DMTr-3-O-erucyl-rac-glycerol-2-O-(2-cyanoethyl)-N,N-diisopropylphosphoramidite To a solution of 1.3 g (1.85 mmol, 701 g/mol) 1-O-DMTr-3-O-erucyl-rac-glycerol and 0.52 ml (0.375 g, 3.71 mmol, 101 g/mol) triethylamine in 15 mL of $CH_2Cl_2$ pre-cooled to 0° C. (ice-water bath) 0.62 mL (0.65 g, 2.78 mmol, 1.061 g/ml, 236.68 g/mol) chloro-2-cyanoethyl-N,N-diisopropyl-phosphoramidite was added. The reaction mixture was allowed to warm (slowly) to room temperature and further was stirred for 2 h. TLC confirmed completion of the reaction Rf=0.45 (starting material—0.25), (AcOEt/hexane=1:5). Additional spot (with DMTr) was seen at start point. Then the mixture was diluted with 40 mL of $CH_2Cl_2$, washed with saturated $NaHCO_3$ (1×50 mL), and then with saturated NaCl (1×50 mL), dried over $Na_2SO_4$, and evaporated to dryness. The mixture of diastereomers was purified by column chromatography using 0-100% hexane-AcOEt as eluent and collecting fractions with Rf=0.45 (AcOEt/hexane=1:5). Yield: 0.71 g (43%).

Example 4: Synthesis of Oligonucleotides with a 5' Lipophilic Modification

All oligonucleotides were synthesized using standard phosphoramidite chemistry (Beaucage, S. L.; Caruthers, M. H. "Deoxynucleoside phosphoramidites—A new class of key intermediates for deoxypolynucleotide synthesis". Tetrahedron Lett., 1981, 22:1859) on a MerMade 192 oligonucleotide synthesizer (BioAutomation) or Oligopilot 10 synthesizer (GE) at 200 to 1000 nmole scales using standard CPG supports (BioSearch) or Glen UnySupport (Glen Research). The DNA, 2'-OMe, 2'-F, and LNA monomers were obtained from ChemGenes Corporation, Exiqon or Glen Research. All phosphoramidites other than DNA were coupled with extended coupling times (e.g. 8 to 15 min for LNA, 2'-O-Methyl, 2'-Fluoro). After synthesis, the oligonucleotides were cleaved from the support and deprotected using AMA (a 50:50 mixture of ammonium hydroxide and aqueous methylamine) at 65° C. for one hour or using aqueous ammonium hydroxide at 55° C. for 8 hours. After coupling of the last nucleotide unit, the DMTr group was cleaved as during chain elongation and then the resulting 5' hydroxyl group was reacted with the phosphorylating agent 1,2-O-Dierucyl-rac-glycerol-3-O-(2-cyanoethyl)-N,N-diisopropylphosphoramidite or 1-O-Erucyl-2-O-myristyl-rac-glycerol-3-O-(2-cyanoethyl)-N,N-diisopropylphosphoramidite from Example 1, respectively, resulting in lipophilic Dier-derivative 105058 or Ermy-derivative 105059, respectively. We compared the lipophilic oligonucleotides in their activity with know lipophilic oligonucleotides shown in Table 2. The crude lipophilic oligonucleotides were purified via DMTr-selective cartridge purification techniques and if necessary further purified via RP HPLC and desalted via cartridge-based methods. Alternatively, they were purified using ion exchange chromatography. The final oligonucleotides were characterized using LC-MS.

TABLE 2

Lipophilic antisense oligonucleotides against ApoB
(Legend: see table 1a and 1b)

| Code | oligonucleotide |
|---|---|
| 102102 | βG*βZ*dA*dT*dT*dG*dG*dT*dA*dT*βT*βZ*βA |
| 101420 | Hex-βG*βZ*dA*dT*dT*dG*dG*dT*dA*dT*βT*βZ*βA |
| 105058 | Dier-βG*βZ*dA*dT*dT*dG*dG*dT*dA*dT*βT*βZ*βA |
| 105059 | Ermy-βG*βZ*dA*dT*dT*dG*dG*dT*dA*dT*βT*βZ*βA |
| 105551 | Chol-βG*βZ*dA*dT*dT*dG*dG*dT*dA*dT*βT*βZ*βA |
| 105553 | Hex-SS-βG*βZ*dA*dT*dT*dG*dG*dT*dA*dT*βT*βZ*βA |
| 105554 | Bat-SS-βG*βZ*dA*dT*dT*dG*dG*dT*dA*dT*βT*βZ*βA |
| 105556 | Dier-SS-βG*βZ*dA*dT*dT*dG*dG*dT*dA*dT*βT*βZ*βA |
| 105557 | Ermy-SS-βG*βZ*dA*dT*dT*dG*dG*dT*dA*dT*βT*βZ*βA |
| 105558 | dRVitA-βG*βZ*dA*dT*dT*dG*dG*dT*dA*dT*βT*βZ*βA |
| 105559 | dRVitA-SS-βG*βZ*dA*dT*dT*dG*dG*dT*dA*dT*βT*βZ*βA |
| 105560 | dRVitE-βG*βZ*dA*dT*dT*dG*dG*dT*dA*dT*βT*βZ*βA |
| 105561 | dRVitE-SS-βG*βZ*dA*dT*dT*dG*dG*dT*dA*dT*βT*βZ*βA |
| 105754 | Dier-βZ*βG*dT*dC*dT*dA*dT*dG*dT*dA*βT*βA*βG (102103 seq) |
| 105755 | DMTr-βG*βZ*dA*dT*dT*dG*dG*dT*dA*dT*βT*βZ*βA |

Example 5: Biological Activity of Lipophilic Antisense Oligonucleotides Against ApoB (A) Cell Culture and Treatment Human hepatocarcinoma cells (Hep3b) were acquired from the "Deutsche Sammlung von Mirkoorganismen and Zellkulturen GmbH" (DSMZ). For the KD studies 3.000-10.000 cells/well were seeded 1-3 days prior treatment into 96 multi-titer plates yielding 70-80% confluence on the day of treatment. For gymnotic delivery, the cells were incubated with indicated concentrations of unformulated ASO in MEM with high Glucose (6 g/l; Invitrogen, Carlsbad, Calif., USA) without L-Glutamine for 8 d.

Following the treatment period mRNA levels of target and reference (housekeeper) mRNA was determined by the Quanti Gene Assay (Affymetrix, Santa Clara, Calif., USA) according to the manufactures standard protocol. Prior to lysis the cell viability was analyzed by Cell Titer Blue Assay (Promega, Madison, Wis., USA). Non-effective, scrambled ASO was used as negative control and reference.

(B) Gene Expression Assay: Branched DNA

QuantiGene 2.0 assay (Affymetrix Inc. Santa Clara, Calif.) was utilized to measure the expression level of target genes before and after LNA Hep3B cells. Human ApoB probes and housekeeping gene PPIB probes were purchased from Affymetrix. Standard assay procedures were carried out according to the manufacturer's recommendations. On the day of harvesting, 200 μl/well of lysis buffer (with 1:100 protease K) was added to the cells. A total of 20 μl lysate was used for human ApoB and PPIB probes respectively. Assay plates were read on the GloRunner Microplate Luminometer (Promega Corp, Sunnyvale, Calif.). The data reported in this study are normalized against housekeeping gene PPIB.
(C) In Vivo Activity in Mice Acute in vivo activity assessments were performed in male and female human mice. Male (22-30 g) and female mice (20-25 g) employed in this study were 10 weeks old and fed regular diet. 2.5 mg/kg were administered subcutaneously or intravenously.

Effects on ApoB expression in the liver were also assessed at study termination and baseline ApoC3 mRNA levels were determined from a group of mice euthanized on Day 0 of the study. Liver lobes were excised immediately after euthanasia and snap frozen in liquid nitrogen. RNA was subsequently isolated and ApoB mRNA expression was determined using the Affymetrix bDNA kit (QuantiGene, Affymetrix). The ApoB mRNA expression was normalized to mouse PPIB, a housekeeper gene, and reported as percent ApoB knockdown (KD) when compared to a PBS-treated control group.

Figure 1A:
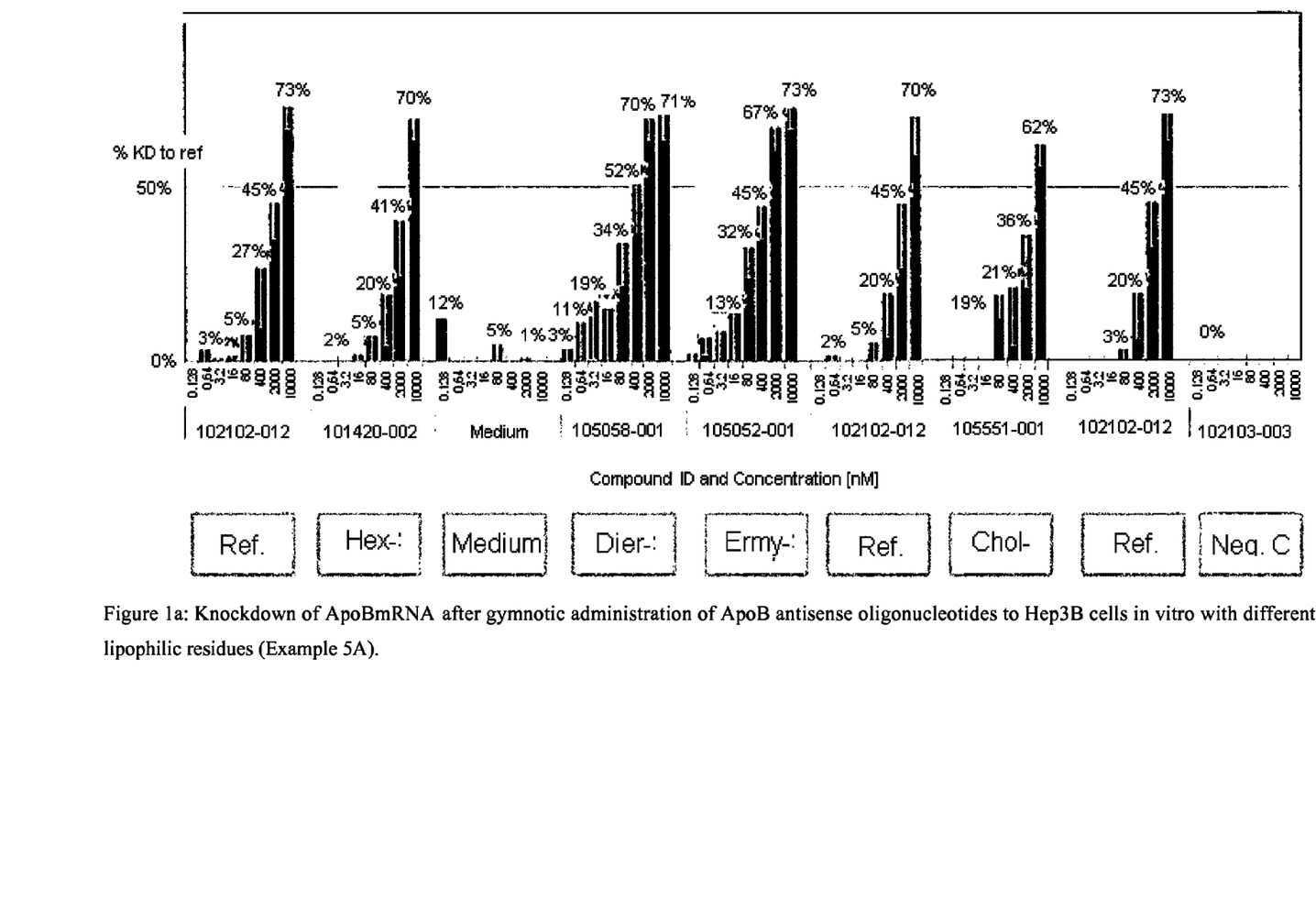
Figure 1a: Knockdown of ApoBmRNA after gymnotic administration of ApoB antisense oligonucleotides to Hep3B cells in vitro with different lipophilic residues (Example 5A).
Figure 1B:
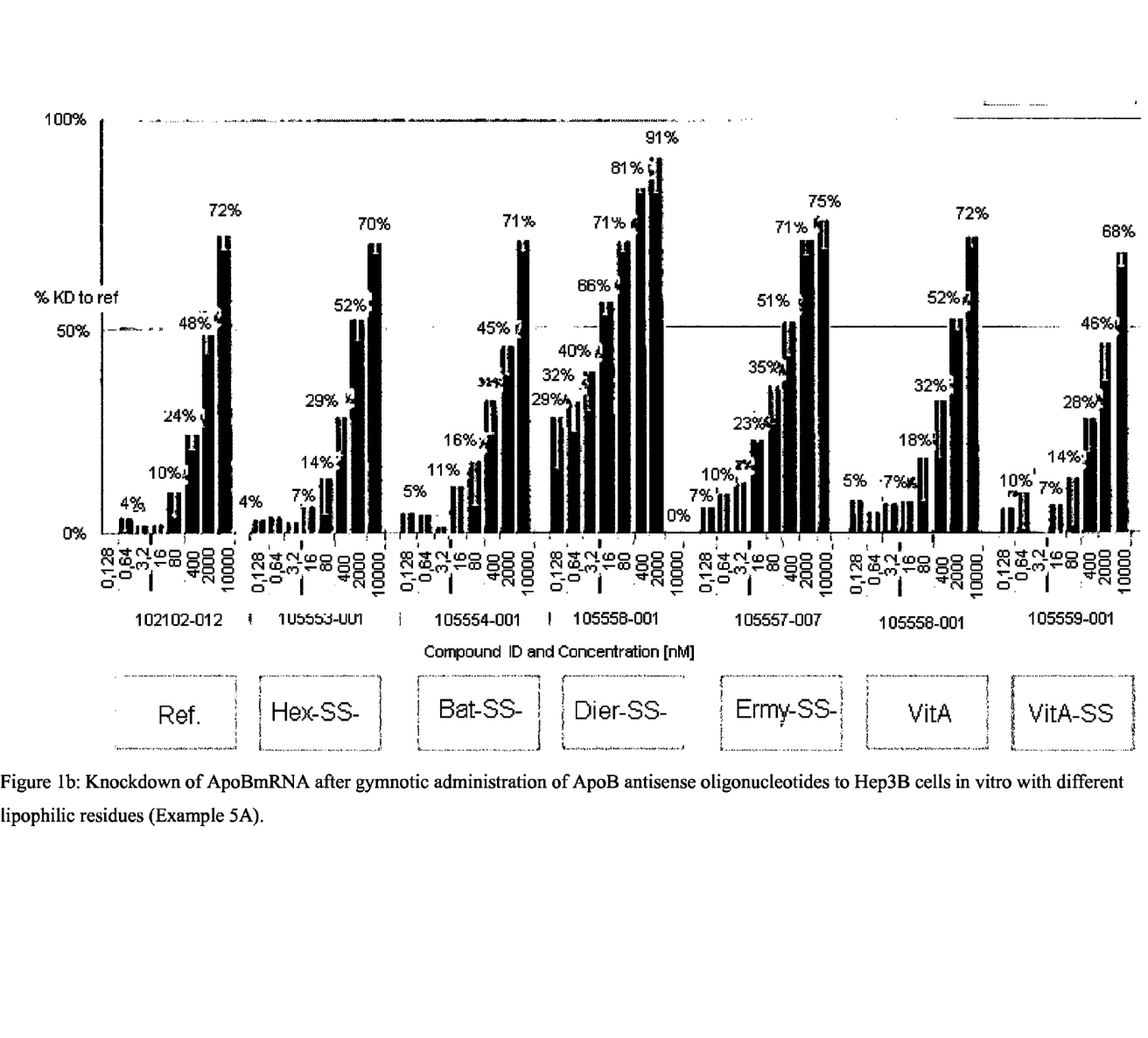
Figure 1b: Knockdown of ApoBmRNA after gymnotic administration of ApoB antisense oligonucleotides to Hep3B cells in vitro with different lipophilic residues (Example 5A).

The antisense oligonucleotide derivative with a dierucylglycerol modification is 105058, which is derived from parent compound 102102, which is identical in sequence and chemical backbone modification, but has no 5'-lipophilic residue. 102102 and 105058 are both directed against ApoB mRNA and efficiently silence ApoB expression in Hep3B cells. Surprisingly we found that 105058 is less active on transfection with Lipofectamine2000 (L2K) but is significantly more active without transfection (gymnotic delivery) as compared the non derivatized parent compound (102102) as depicted in FIGS. 1a and 1b (example 5A). Since the administration of antisense ODN in vivo is also done without a transfection agent and efficacy of gymnotic antisense delivery correlates well with the in vivo target KD, the lipophilic analog 105058 is a more promising antisense agent. Furthermore, if the lipophilic dier residue is bound to the 5' end of the antisense oligonucleotide via a disulfide linker (105556) there is more efficient KD of ApoB mRNA as compared to the antisense oligonucleotide in which the lipophilic dier residue is directly linked to the 5' end of the oligonucleotide (105058). Therefore, the use of a reversible linker, such as a disulfide linker, appears to be beneficial for efficient KD.

Figure 2:
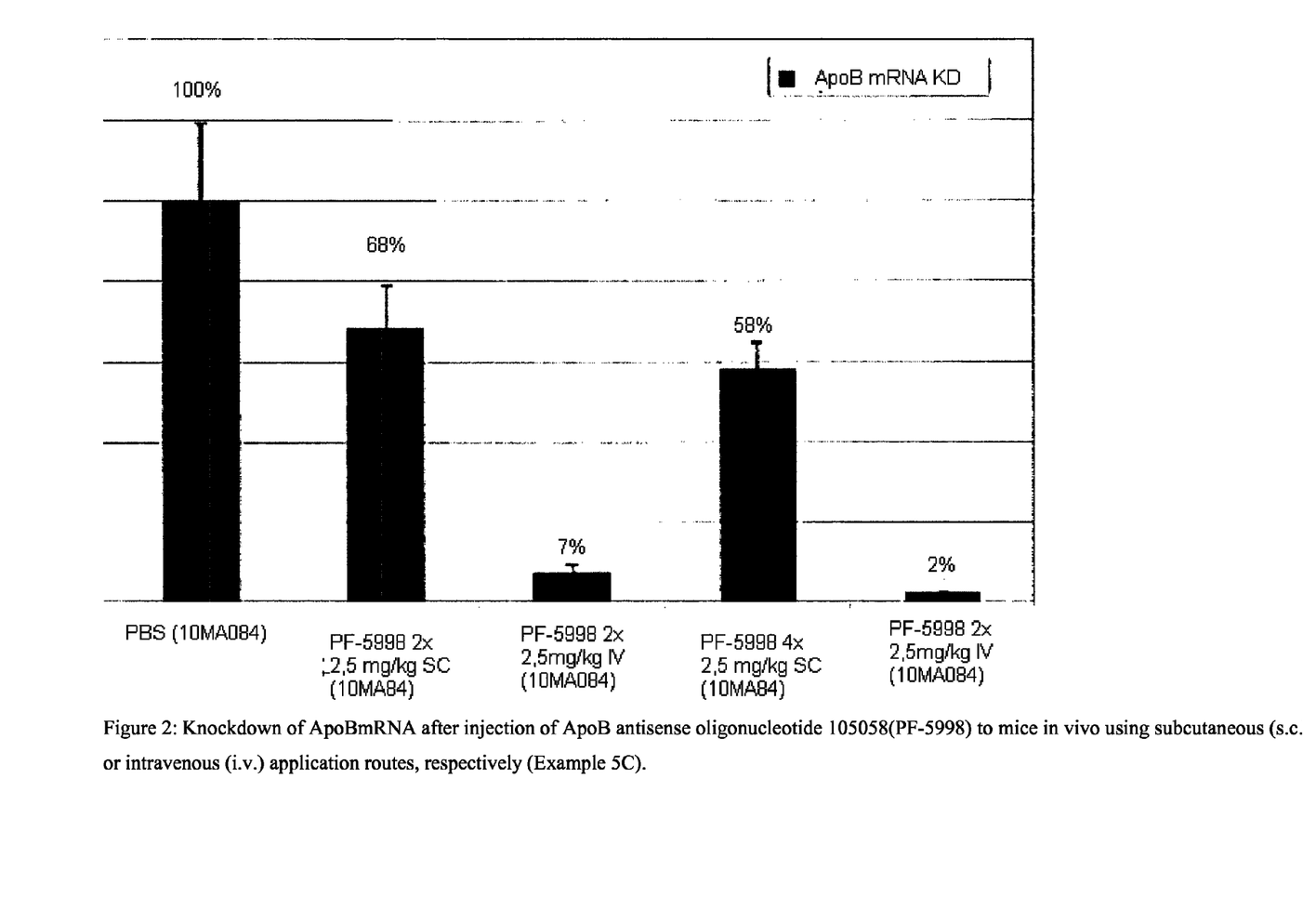
Figure 2: Knockdown of ApoBmRNA after injection of ApoB antisense oligonucleotide 105058(PF-5998) to mice in vivo using subcutaneous (s.c.) or intravenous (i.v.) application routes, respectively (Example 5C).

We found that the lipophilic 5' dier conjugate is a effective in ApoB KD in CD1 mice (example 5c). The type of administration plays an important role in that the i.v. route leads to much better KD of ApoB in liver than the s.c. route of administration (FIG. 2). We believe that the lower activity of s.c. injection is due to retention of the ODN at the injections site and less lipophilic gapmer reaches the liver. Therefore, we hypothesize that lipophilic gapmers are also very efficient for local administration, e.g. intradermal injection for inhibition of skin targets or intratumoral injection for inhibition of tumor targets, such as in melanoma.

Example 6: Biological Activity of Lipophilic Antisense Oligonucleotides Against Beta-2 Microglobulin The following oligonucleotides (table 3) were synthesized according to Examples 1 to 4 and evaluated in the KD activity against beta-2 microglobulin (B2M) targets

TABLE 3

Lipophilic antisense oligonucleotides against beta-2 microglobulin
(Legend: see table 1a and 1b)

| Code | Oligonucleotide |
|---|---|
| MB-00027 | βA*βG*dT*dT*dG*dC*dC*dA*dG*dC*dC*dC*dT*βZ*βZ |
| MB-00540 | Eru*SS*βA*βG*dT*dT*dG*dC*dC*dA*dG*dC*dC*dC*dT*βZ*βZ |
| MB-00541 | Myr*SS*βA*βG*dT*dT*dG*dC*dC*dA*dG*dC*dC*dC*dT*βZ*βZ |
| MB-00542 | Dier*SS*βA*βG*dT*dT*dG*dC*dC*dA*dG*dC*dC*dC*dT*βZ*βZ |
| MB-00543 | Ermy*SS*βA*βG*dT*dT*dG*dC*dC*dA*dG*dC*dC*dC*dT*βZ*βZ |

(A) Cell Culture and Treatment

Human newborn foreskin fibroblast cells (BJ) were acquired from the Stemgent (Cambridge, Mass., USA). 3.000 cells/well were seeded 2 days prior treatment into 48 well plates. For gymnotic delivery, the cells were incubated with indicated concentrations of unformulated ASO in DMEM for 9 d.
(B) Analysis of Beta-2 Microglobulin Expression on the Cell Surface.

Following the treatment period protein levels of B2M were determined by monoclonal antibody staining against cell surface beta-2 microglobulin. Cells were trypsinized, washed and resuspended with PBS-BSA. Cells were stained with a monoclonal anti-beta-2 microglobulin antibody conjugated to Phytoerythrin (beta-2 microglobulin-PE). Cells were measured by flow cytometry and gated for B2M negative fractions. Knock down activity of the unmodified ASO was set to 1 for each concentration and relative activity of the modified ASO was calculated.

In this example we used primary cells (human newborn fibroblasts) and an antisense oligonucleotide targeting beta-2 microglobulin, a component present in MHC classI complex.

Figure 3:
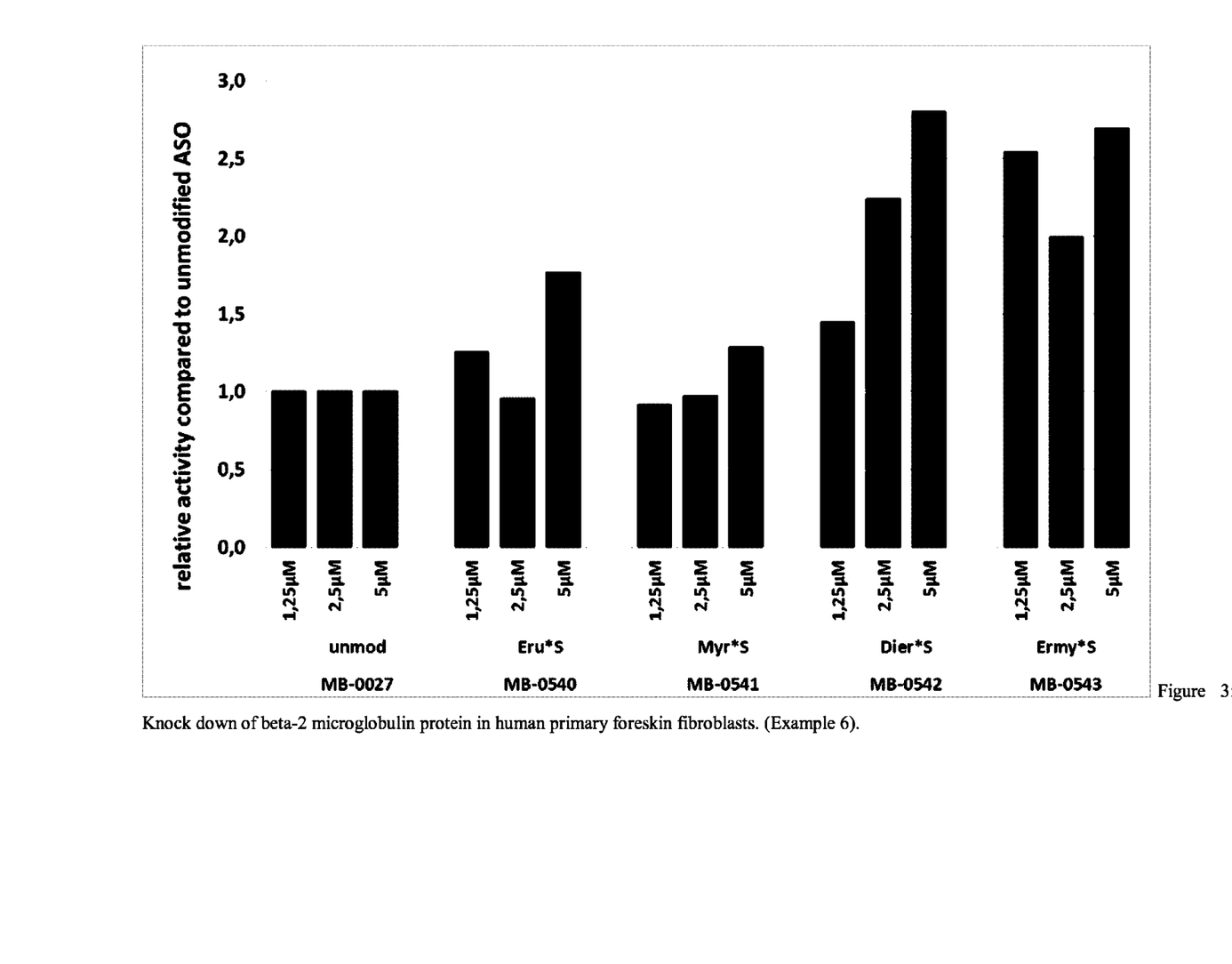

FIG. 3 shows the knock down activity of the unmodified parent sequence (MB-00027) with antisense oligonucleotides modified with only one lipophilic residue "Eru*S" (MB-00540) and Myr*S (MB-00541) with antisense oligonucleotides modified with a combination of these two lipophilic residues "Dier*S" (MB-00542) and "Ermy*S" (MB-00543). All antisense oligonucleotides were delivered by gymnotic delivery (no transfection reagent).

Surprisingly, we found that both double-modified Antisense oligonucleotides "Dier*S" (MB-00542) and "Ermy*S" (MB-00543) are up to 2.5 fold as active as the unmodified compound. The double modified compounds are also up to 2.5 fold more active compared to the compounds modified with only a single lipophilic residue.

The invention claimed is:
1. A lipophilic oligonucleotide comprising a phosphate glycerol unit containing at least one aliphatic unsaturated carbon bond according to formula I

Formula I with

Oligonucleotide=an unmodified or modified nucleic acid of 2-1000 nucleotides in length

R=a bond or a linker unit

Y=OH, SH or NH substituted with one residue comprising hydrogen or branched or unbranched and/or substituted or unsubstituted alkyl, aryl and/or alkyl aryl residue with 10 to 30 carbon atoms X and Z=independently O, S or N, substituted with one residue comprising hydrogen or branched or unbranched and/or substituted or unsubstituted alkyl, aryl and/or alkyl aryl residue with 10 to 30 carbon atoms

R1, R2=branched or unbranched and/or substituted or unsubstituted alkyl, aryl and/or alkylaryl residue with 10 to 30 carbon atoms, with the proviso that at least one of the residues R1 or R2 comprises at least one aliphatic carbon-carbon double bond.

2. Lipophilic oligonucleotide according to claim 1 as defined in Formula III wherein R, X, Y, Z, R1, and R2 have the same meaning as in Formula I and ODN stands as abbreviation for oligonucleotide with the same meaning as in Formula I.

3. Lipophilic oligonucleotide according to claim 1 as defined in Formula IV wherein R, X, Y, Z, R1, R2 have the same meaning as in Formula I and ODN stands as abbreviation for oligonucleotide with the same meaning as in Formula I.

4. A lipophilic oligonucleotide according to claim 1 wherein R is a bifunctional linker unit and is selected from the group
branched or unbranched and/or substituted or unsubstituted alkyl, aryl and/or alkyl aryl residue with 1 to 100 carbon atoms
sugar
amino-, thiol-, ethylene glycol-, in particular, triethyleneglycol and hexaethyleneglycol modified C3-, C-6 and C-12-linkers optionally having two functional groups, such as e.g. amino-, thiol-, carboxyl or hydroxyl functions which allow attachment of an oligonucleotide on one side and a lipophilic residue on the other side
reversible linker, which can be designed to undergo a chemical or enzymatic cleavage reaction.

5. Method for the preparation of oligonucleotides of claim 1, wherein Oligonucleotide-R—OH is coupled with a phosphate glycerol unit containing one lipophilic residue according to formula II Formula II With

R5, R6=Methyl, Ethyl, Propyl, isopropyl, Butyl residue, or R1 and R2 forming a cyclic aliphatic residue R4=protecting group, selected from the group of alkyl, substituted alkyl, alkylaryl, and β-cyanoalkyl R1 and R2=same meaning as in Formula I and subsequently oxidized and deprotected to yield oligonucleotides of formula I.

6. Method according to claim 5 wherein a compound according to formula VI is used as phosphate glycerol unit containing one lipophilic residue

VI

With

R5, R6=Methyl, Ethyl, Propyl, isopropyl, Butyl residue, or R1 and R2 forming a cyclic aliphatic residue R4=protecting group, selected from the group of alkyl, substituted alkyl, alkylaryl, β-cyanoalkyl, β-phenylethyl.

7. The method according to claim 5 wherein a compound according to formula VII is used as phosphate glycerol unit containing one lipophilic residue

VII

With

R5, R6=Methyl, Ethyl, Propyl, isopropyl, Butyl residue, or R1 and R2 forming a cyclic aliphatic residue R4=protecting group, selected from the group of alkyl, substituted alkyl, alkylaryl, β-cyanoalkyl, β-phenylethyl.

8. The method according to claim 5, wherein a compound according to formula VIII is used as phosphate glycerol unit containing one lipophilic residue

VIII with DMTr=4,4'-Dimethoxytrityl residue.

* * * * *